United States Patent
Maiorino

(10) Patent No.: US 8,333,788 B2
(45) Date of Patent: Dec. 18, 2012

(54) KNOTTED SUTURE END EFFECTOR

(75) Inventor: Nicholas Maiorino, Branford, CT (US)

(73) Assignee: Covidien LP, Mansfield, MA (US)

( * ) Notice: Subject to any disclaimer, the term of this patent is extended or adjusted under 35 U.S.C. 154(b) by 310 days.

(21) Appl. No.: 12/571,806

(22) Filed: Oct. 1, 2009

(65) Prior Publication Data

US 2010/0094337 A1    Apr. 15, 2010

Related U.S. Application Data

(60) Provisional application No. 61/104,085, filed on Oct. 9, 2008.

(51) Int. Cl.
*A61B 17/04* (2006.01)
(52) U.S. Cl. .......................... 606/228; 606/232
(58) Field of Classification Search .......... 606/228–233, 606/148, 139; 289/17, 1.2, 3, 4
See application file for complete search history.

(56) References Cited

U.S. PATENT DOCUMENTS

| | | | |
|---|---|---|---|
| 2,646,298 A * | 7/1953 | Leary | 289/1.2 |
| 3,580,256 A | 5/1971 | Wilkinson | |
| 3,664,345 A | 5/1972 | Dabbs et al. | |
| 4,669,473 A | 6/1987 | Richards et al. | |
| 4,741,330 A | 5/1988 | Hayhurst | |
| 4,898,156 A | 2/1990 | Gatturna et al. | |
| 4,901,721 A | 2/1990 | Hakki | |
| 4,950,285 A | 8/1990 | Wilk | |
| 5,041,129 A | 8/1991 | Hayhurst et al. | |
| 5,178,629 A | 1/1993 | Kammerer | |
| 5,312,436 A | 5/1994 | Coffey et al. | |
| 5,464,425 A | 11/1995 | Skiba | |
| 5,573,286 A | 11/1996 | Rogozinski | |
| 5,628,756 A | 5/1997 | Barker, Jr. et al. | |
| 5,728,109 A * | 3/1998 | Schulze et al. | 606/139 |
| 5,769,862 A | 6/1998 | Kammerer et al. | |
| 5,865,836 A | 2/1999 | Miller | |
| 6,596,014 B2 | 7/2003 | Levinson et al. | |
| 6,596,015 B1 * | 7/2003 | Pitt et al. | 606/232 |
| 6,626,919 B1 | 9/2003 | Swanstrom | |
| 7,220,265 B2 * | 5/2007 | Chanduszko et al. | 606/139 |
| 2002/0095165 A1 | 7/2002 | Chan | |
| 2002/0165561 A1 | 11/2002 | Ainsworth et al. | |
| 2003/0149447 A1 | 8/2003 | Morency et al. | |
| 2004/0260343 A1 | 12/2004 | Leclair | |
| 2005/0267531 A1 | 12/2005 | Ruff et al. | |
| 2006/0116718 A1 | 6/2006 | Leiboff | |
| 2006/0229675 A1 | 10/2006 | Novoa et al. | |
| 2007/0203511 A1 | 8/2007 | Vardi | |
| 2008/0294193 A1 | 11/2008 | Schwartz et al. | |

FOREIGN PATENT DOCUMENTS

DE   2900265 A1   7/1980

(Continued)

OTHER PUBLICATIONS

European Search Report in European Application No. EP10 25 1485 dated Dec. 6, 2010.

(Continued)

*Primary Examiner* — Julian Woo

(57) ABSTRACT

A suture including a knotted end effector is provided. The suture includes a body portion defining a longitudinal axis and an end effector integrally formed from the body portion. The end effector includes first and second extensions extending outwardly from the longitudinal axis in opposite directions. Each of the first and second extensions includes at least one throw.

9 Claims, 7 Drawing Sheets

FOREIGN PATENT DOCUMENTS

| | | |
|---|---|---|
| EP | 1946705 A2 | 7/2008 |
| WO | WO 00/57796 A1 | 10/2000 |
| WO | WO 02/094106 A1 | 11/2002 |
| WO | WO 03/088818 A2 | 10/2003 |
| WO | WO 2004/004577 A1 | 1/2004 |
| WO | WO2006111394 A2 | 10/2006 |
| WO | WO 2009/087105 A1 | 7/2009 |

OTHER PUBLICATIONS

European Search Report for EP 09252392.7-2310 date of completion is Feb. 15, 2010 (3 pages).

European Search Report for EP 11250356.0-1269 date of completion is Jun. 20, 2011 (3 pages).

* cited by examiner

KNOTTED SUTURE END EFFECTOR

CROSS-REFERENCE TO RELATED APPLICATION

The present application claims benefit of and priority to U.S. Provisional Application No. 61/104,085, filed Oct. 9, 2008, the entire disclosure of which is incorporated herein by reference.

BACKGROUND

1. Technical Field

The present disclosure relates to sutures for use in medical procedures. More particularly, the present disclosure relates to a knotted end effector for a suture.

2. Background of Related Art

Medical sutures may be formed from a variety of materials and may be configured for use in limitless applications. The proximal end of the suture may have a sharpened tip or may include a needle for penetrating tissue. A distal end of the suture may include an anchor or end effector for maintaining the suture in engagement with the tissue as the suture is pulled through the tissue. End effectors are available in many size and configurations. Typically, an end effector is formed independently of the suture and is later attached to the distal end of the suture.

In many instances, a clinician may prefer to tie a knot in the suture to anchor the suture within the tissue. Although the clinician may find this practice convenient, the knot formed on the end of the tissue is not always suitable to prevent the suture from being pulled through the tissue, for example, when the knot slips or is too small to engage the tissue. Additionally, the tying of a knot, especially with the fine suture material required for use in many procedures, is tedious and time consuming.

Therefore, a continuing need exists for a knotted end effector and a method of making a knotted end effector.

SUMMARY

Accordingly, a suture including a knotted end effector is provided. The suture includes a body portion defining a longitudinal axis and an end effector integrally formed from the body portion. The end effector includes first and second extensions extending outwardly from the longitudinal axis in opposite directions. Each of the first and second extensions include at least one throw. The end effector may be substantially perpendicular to the longitudinal axis. The first and second extensions may include a plurality of throws. The first and/or second extension may include three (3) throws. The end effector may include substantially T-shape and may be formed on a distal end of the body portion.

Also provided is a method of forming an end effector. The method includes the steps of providing a length of suture, crossing a first end of the suture over a second end of a suture to form a first loop, wrapping the first end of the suture around the suture within the first loop "n" number of times, placing the suture about a fixture between the first loop and the first end, wrapping the first end of the suture around the fixture to form a second loop, wrapping the first end of the suture around the suture within the first loop "m" number of times, pulling the first and second ends in opposite directions to tighten the first and second loops about the fixture, threading the first end of the suture through the second loop to form a third loop, threading the second end of the suture through the second loop to form a third loop, removing the suture from the fixture, pulling the third and fourth loops in opposite directions to tighten the first and second loops and pulling the first and second ends of the suture in opposite directions to tighten the third and fourth loops.

The method may further include the step of trimming the first end of the suture. The fixture may include a channel for receiving first and second ends of the suture. The step of threading the first end of the suture through the second loop may be performed from the top down or from the bottom up. The step of threading the second end of the suture through the second loop may be performed from the top down or from the bottom up. Variables "n" and "m" may be equal or different. In one embodiment, variables "n" and "m" may equal three (3).

Further provided is a suture including a body portion defining a longitudinal axis and an end effector integrally formed from the body portion. The end effector includes first and second extensions extending perpendicular to the longitudinal axis in opposite directions. Each of the first and second extensions are undulated. The first and second extensions may each include a plurality of throws.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 2:
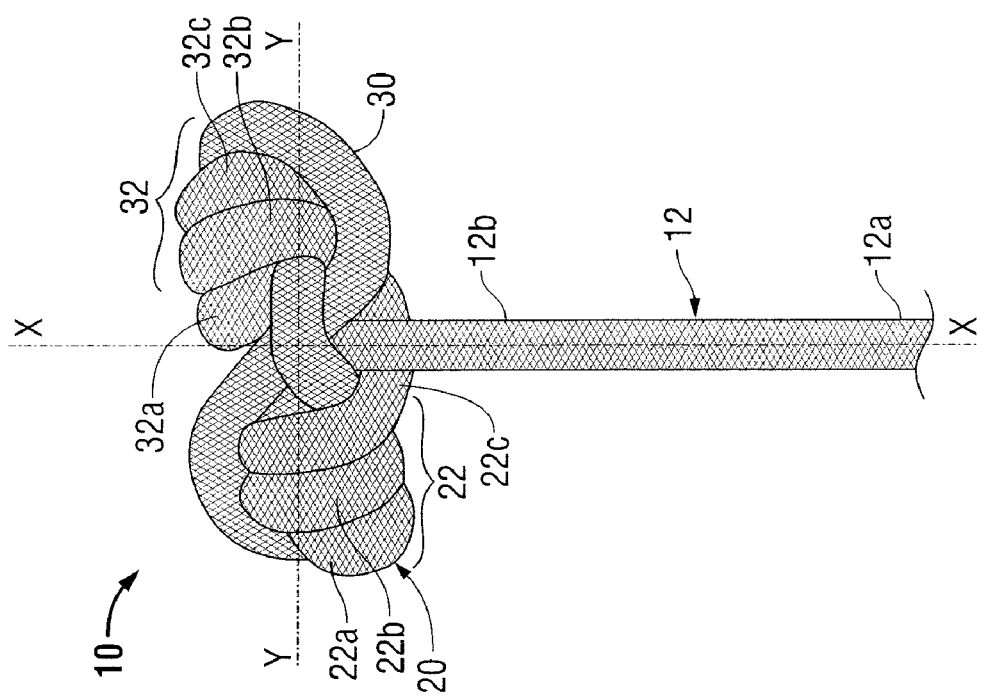
FIG. 2 is a front view of the end effector of FIG. 1.
Figure 1:
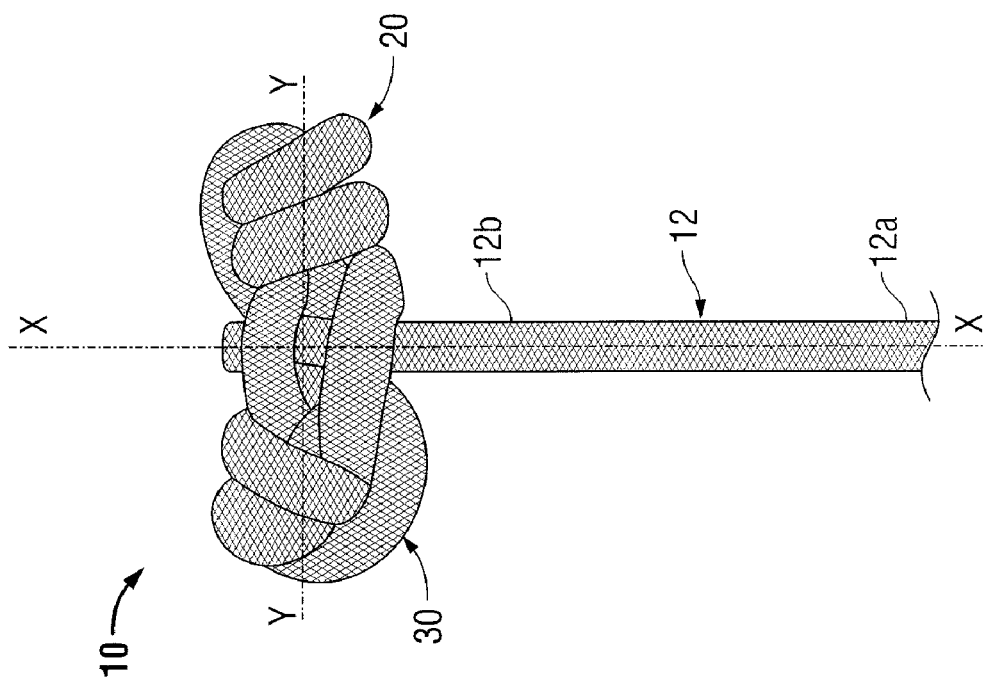
FIG. 1 is a back view of an end effector according to an embodiment of the present disclosure.

Referring initially to FIGS. 1 and 2, an embodiment of an end effector according to the present disclosure is shown generally as end effector 10. Although, as shown, end effector 10 is formed on a distal end 12b of suture 12, end effector 10 may be formed anywhere along the length of suture 12.

Suture 12 may be formed of degradable materials, non-degradable materials, and combinations thereof. More particularly, suture 12 may be formed of a degradable material selected from the group consisting of polyesters, polyorthoesters, polymer drugs, polydroxybutyrates, lactones, proteins, cat gut, collagens, carbonates, homopolymers thereof, copolymers thereof, and combinations thereof. In other embodiments, suitable degradable materials which may be utilized to form suture 12 include natural collagenous materials or synthetic resins including those derived from alkylene carbonates such as trimethylene carbonate, tetramethylene carbonate, and the like; caprolactone; dioxanone; glycolic acid; lactic acid; homopolymers thereof; copolymers thereof; and combinations thereof. In some embodiments, glycolide and lactide based polyesters, especially copolymers of glycolide and lactide, may be utilized to form suture 12.

Suitable non-degradable materials which may be utilized to form suture 12 include polyolefins, such as polyethylene and polypropylene; copolymers of polyethylene and polypropylene, and blends of polyethylene and polypropylene; polyamides (such as nylon); polyamines; polyimines; polyesters such as polyethylene terephthalate; polytetrafluoroethylene; polyether-esters such as polybutester; polytetramethylene ether glycol; 1,4-butanediol; polyurethanes; and combinations thereof. Other suitable non-degradable materials include silk, cotton, linen, carbon fibers, and the like. The polypropylene may be isotactic polypropylene or a mixture of isotactic and syndiotactic or atactic polypropylene.

Suture 12 may be formed using any technique within the purview of those skilled in the art, such as, for example, extrusion, molding and/or gel spinning. In some embodiments, suture 12 may include a yarn made of more than one filament, which may contain multiple filaments of the same or different materials. Where suture 12 is made of multiple filaments, suture 12 may be made using any known technique such as, for example, braiding, weaving or knitting. Suture 12 may also be combined to produce a non-woven suture. Suture 12 may be drawn, oriented, crinkled, twisted, commingled or air entangled to form yarns as part of the suture forming process. In one embodiment, a multifilament suture may be produced by braiding. The braiding may be done by any method within the purview of those skilled in the art.

With reference still to FIGS. 1 and 2, end effector 10 is configured to prevent complete reception of suture 12 through tissue or other material. End effector 10 fauns a substantially T-shaped knot formed on distal end 12b of suture 12. End effector 10 defines an axis "Y" extending perpendicular to a longitudinal axis "X" of suture 12. End effector 10 includes first and second extensions 20, 30 extending perpendicularly from suture 12 in opposite directions along axis "Y" to form a T-shape. Each of first and second extension 20, 30 is formed from a plurality of throws 22a-c, 32a-c, respectively, thereby forming undulated members. As used herein, a throw is defined as an at least three-hundred and sixty degree (360° wrapping or weaving of two limbs and undulated is defined as having a wavelike or rippled form. As shown, first and second extensions 20, 30 each include three throws 22a-c, 32a-c, respectively. It is envisioned, however, that first and second extensions 20, 30 may include any number of throws 22, 32, respectively. It is further envisioned that the number of throws on first extension 20 does not need to be equal to the number of throws on second extension 30. A proximal end 12a of suture 12 may include one or more needles (not shown) and/or may include one or more barbs.

Figure 3:
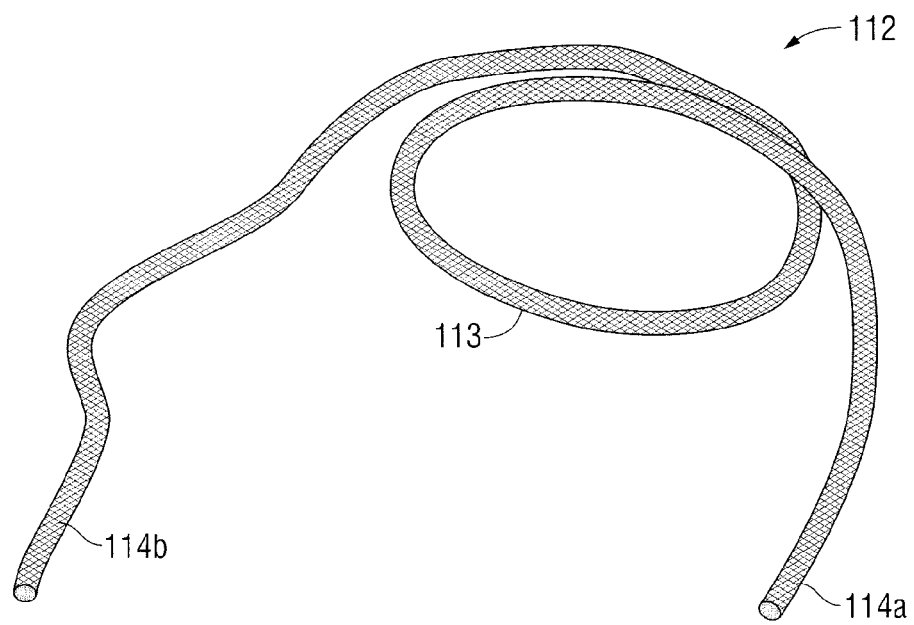
FIGS. 3-15 show sequential steps of a method of forming the end effector of FIGS. 1 and 2.

The method of forming end effector 10 will now be described with reference to FIGS. 3-15. Referring initially to FIG. 3, suture 112 is cut to a desired length. The length of the suture may vary depending on the application for which suture 112 is being used. The size of end effector 110 may also affects the length of suture 112. The more throws 122, 132 (FIG. 15) formed in respective extension 120, 130 of end effector 110, the greater the length or size required of suture 112. The thickness of suture 112 also affects length of suture 112. Alternatively, suture 112 may be formed on the free end of a spool of thread (not shown) and cut to length following the forming of end effector 10. A first, short end 114a of suture 112 is then crossed over a second, long end 114b of suture 112 to form a first loop 113. First loop 113 should be of sufficient size to permit wrapping of first end 114a through first loop 113 multiple times. Although "short" and "long" are used to refer to first and second ends 114a, 114b, respectively, in some embodiments, short end 114a may actually be of equal or longer length than long end 114b.

Figure 4:
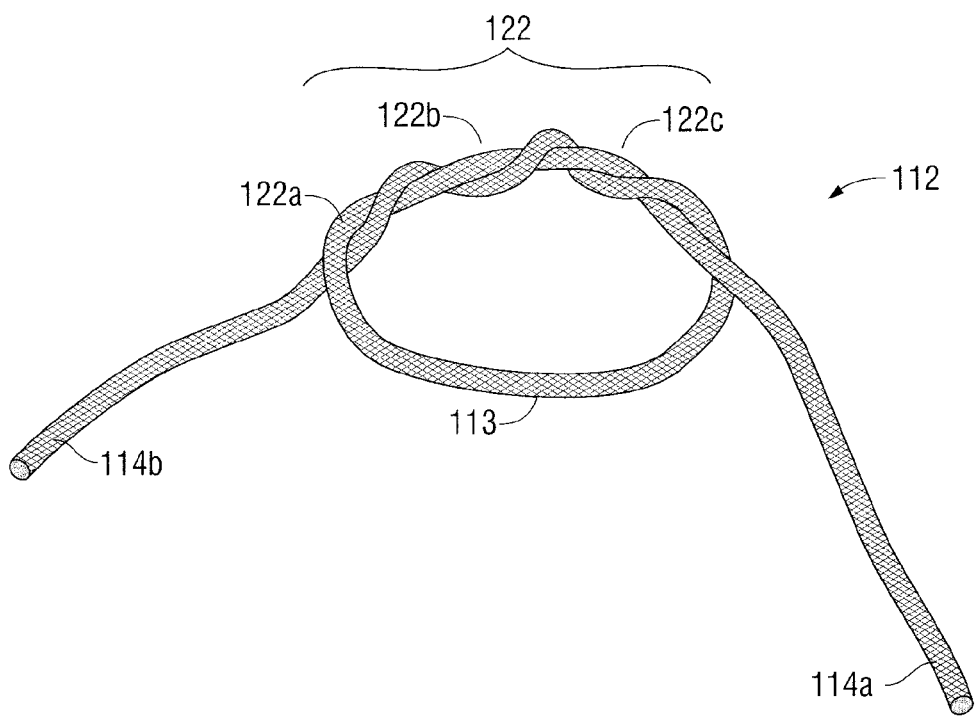

Turning to FIG. 4, first end 114a of suture 112 is then wrapped around suture 112 within loop 113 "n" number of times to form "n" number of throws 122. As shown, first end 114a is wrapped around suture 112 (3) three times to form three (3) throws 122a-c. As discussed above, first end 114a of suture 112 may be wrapped around suture 112 within loop 113 more or less than three (3) times.

Figure 5:
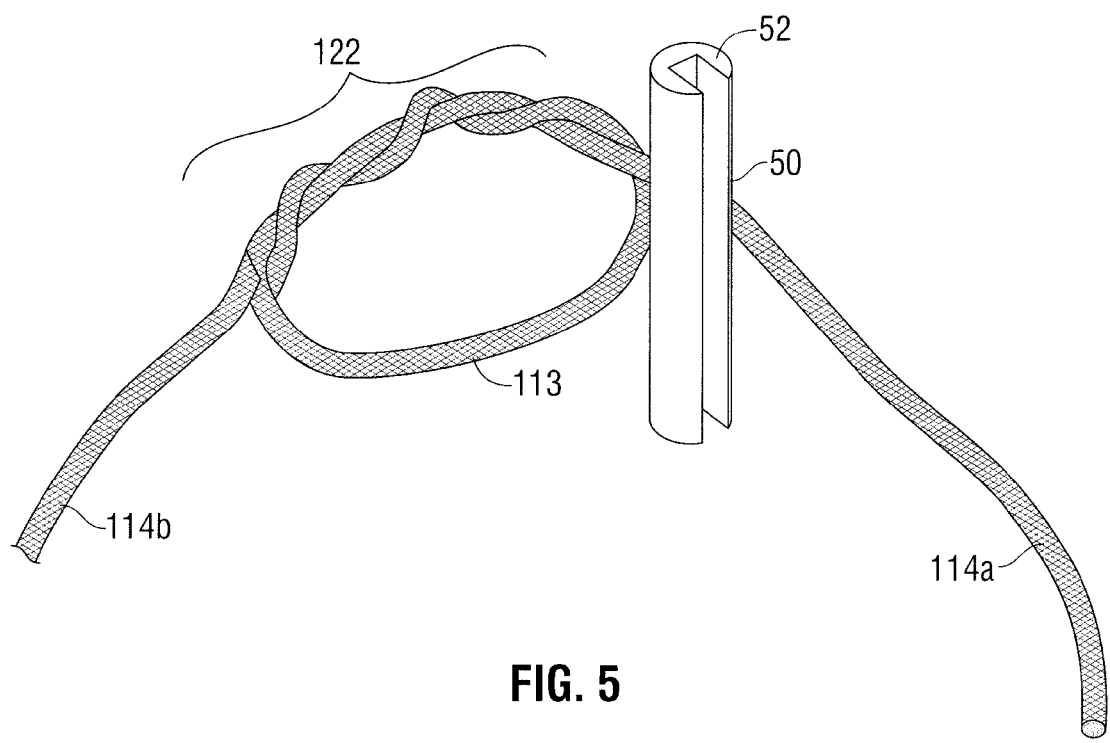

With reference now to FIG. 5, first loop 113 is next placed adjacent to a fixture 50, with fixture 50 being received in the V-shaped notch between first loop 113 and first end 114a. As will be discussed in further detail below, fixture 50 includes a channel 52 extending along a length thereof.

Figure 6:
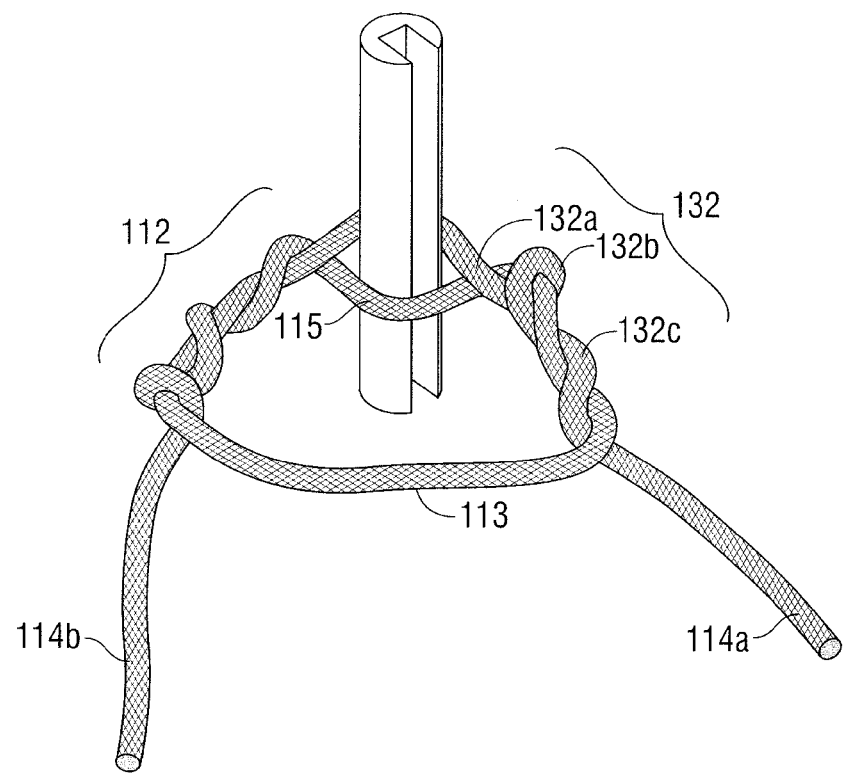

Turning to FIG. 6, first end 114a of suture 112 is next wrapped around fixture 50 to form a second loop 115. First end 114a is then wrapped around suture 112 within loop 113 "m" number of times to form "m" number of throws 132. As shown, first end 114a is wrapped around suture 112 three (3) times to form three (3) throws 132a-c. As discussed above, first end 114a may be wrapped around suture 112 more or less than three (3) times and does not need to be equal to "n" number of throws 122 formed on the opposite side of first loop 113.

Figure 7:
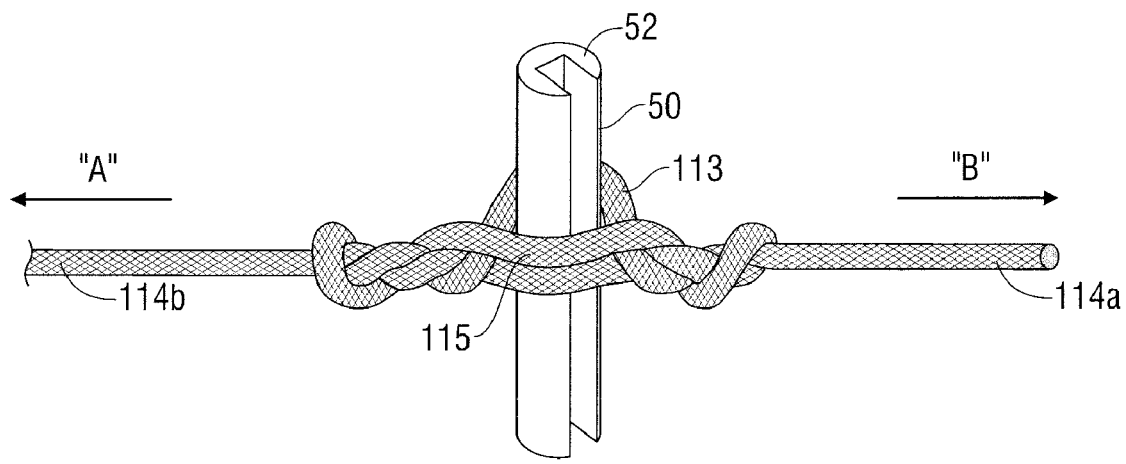
Figure 8:
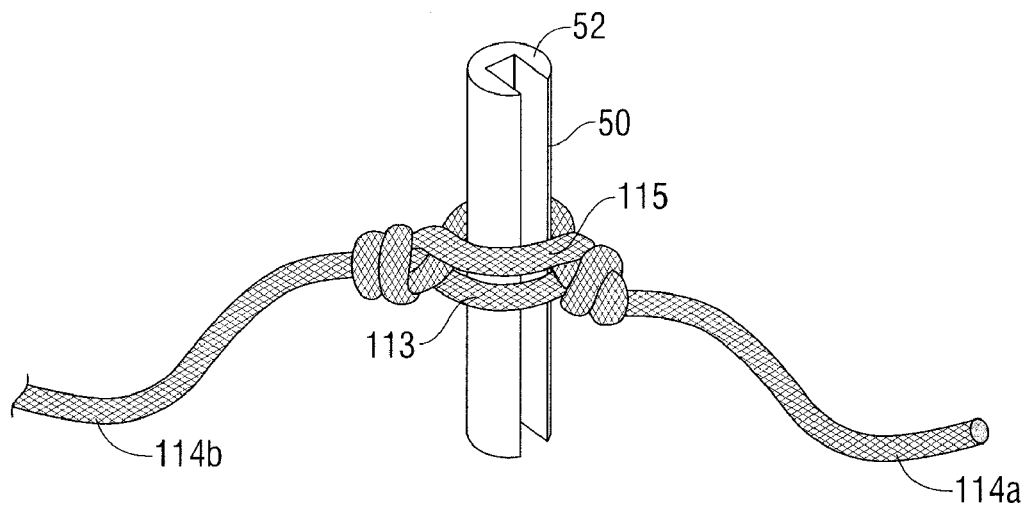

With reference now to FIGS. 7 and 8, first and second ends 114a, 114b of suture 112 are next pulled in opposing directions, as indicated by arrows "A" and "B" (FIG. 7), thereby tightening first and second loops 113, 115 about fixture 50 (FIG. 8).

Figure 9:
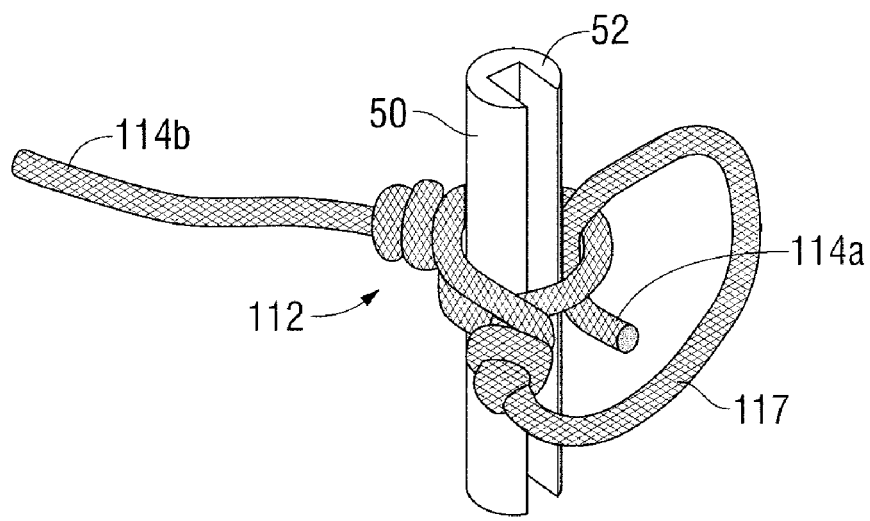

As noted above, fixture 50 includes a channel 52 formed along a length thereof to permit the passage of suture ends 114a, 114b through second loop 115. With reference now to FIG. 9, first end 114a of suture 112 is threaded through second loop 115 by passing first end 114a through channel 52 of fixture 50. It is envisioned, however, that the threading of first end 114a through second loop 115 may accomplished without the use and/or presence of channel 52. First end 114a is threaded through second loop 115 from the top, as shown, to form a third loop 117. In an alternative embodiment, first end 114a of suture 112 may be threaded through second loop 115 from the bottom.

Figure 10:
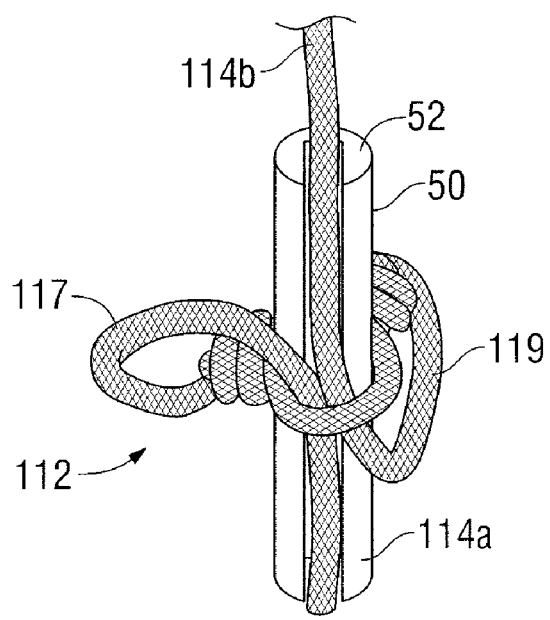

Referring now to FIG. 10, second end 114b of suture 112 is next threaded through second loop 115, through channel 52, if present, in a direction opposite to that which first end 114a was threaded. As shown, second end 114b of suture 112 is threaded through second loop 115 from the bottom up to form a fourth loop 119. In another embodiment, second end 114b may be fed through second loop 115 in the same direction that first end 114a was threaded through second loop 115. In this manner, second end 114b is threaded through second loop 115 from the top down. The direction from which short and long ends 114a, 114b are threaded through second loop 115 determines the final configuration of end effector 110. In yet another embodiment, second end 114b may be threaded through second loop 115 from the top down or the bottom up, and short end 114b may be severed adjacent to outer throw 132c without short end 112 being threading through second loop 115.

Figure 11:
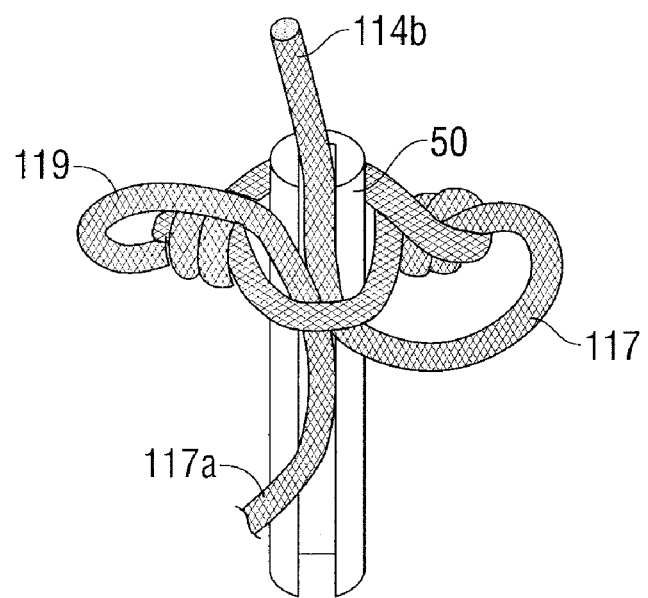
Figure 12:
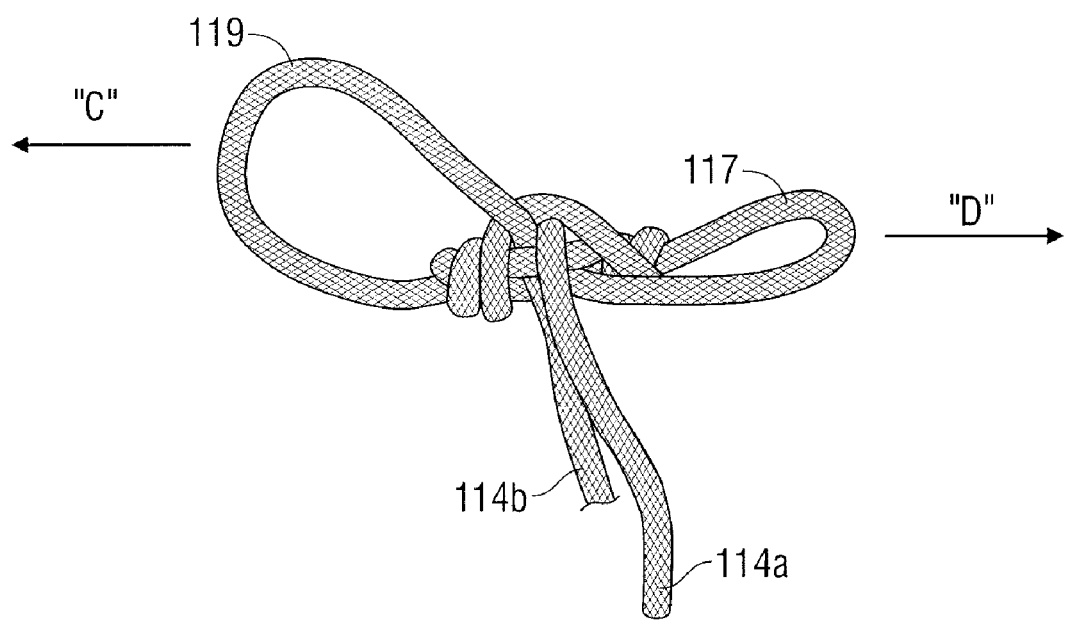

With reference to FIGS. 11 and 12, suture 112 is next removed from fixture 50 (FIG. 10) and third and fourth loops 117, 119 are then pulled in opposite directions (FIG. 11) along an axis perpendicular to the longitudinal axis of suture 112, as indicated by arrows "C" and "D", to tighten first and second loops 113, 115 about short and long ends 114a, 114b.

Figure 13:
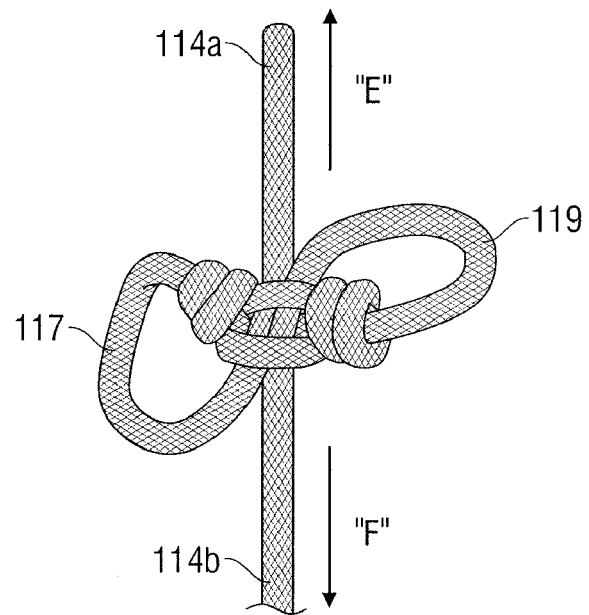

Turning now to FIG. 13, next short and long ends 114a, 114b are pulled in opposite directions, as indicated by arrows "E" and "F," to tighten third and fourth loops 117, 119 about respective throws 122a-c, 132a-c.

Figure 14:
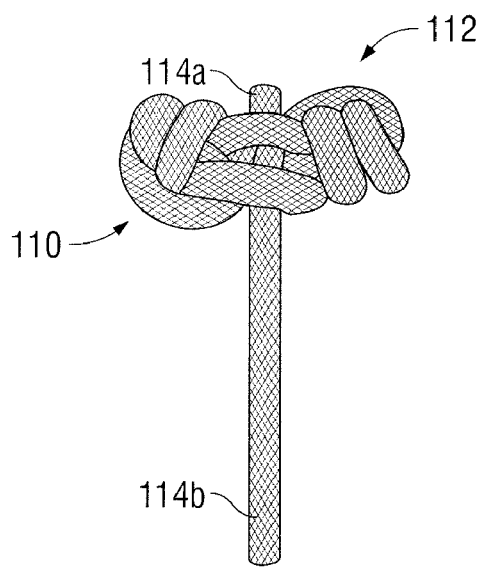
Figure 15:
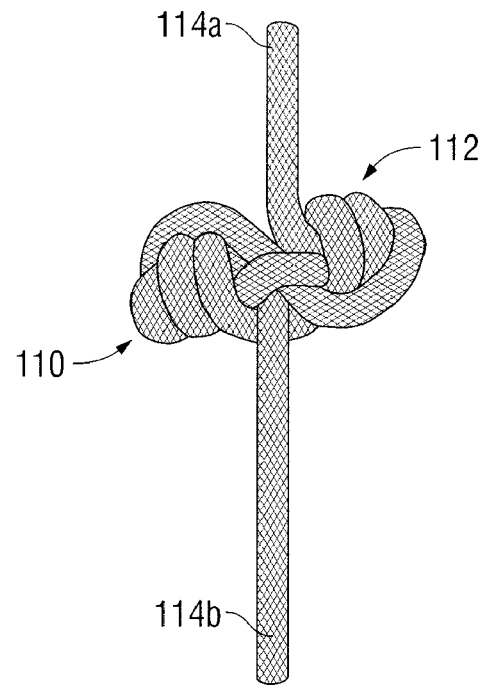

With reference now to FIGS. 14 and 15, first end 114a may then be cut as close to or as far from end effector 110 as desired. In an alternative embodiment, first end 114a may be left uncut, thereby providing a clinician with a means for retracting suture 112.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, it is envisioned that suture 12 may include a loop formed a distal of end effector 10 to permit withdrawal of suture 12 from within tissue.

What is claimed is:

1. A suture comprising:
a body portion defining a longitudinal axis and including a needle on a first end thereof; and
an end effector integrally formed from a second end of the body portion, the end effector including first and second extensions extending outwardly from the longitudinal axis in opposite directions, wherein each of the first and second extensions includes a plurality of throws and the first extension is configured substantially identically to the second extension and, wherein each of the throws defines a central axis that is perpendicular to the longitudinal axis of the body portion.

2. The suture of claim 1, wherein the first and second extensions include a plurality of throws.

3. The suture of claim 1, wherein the first extension includes three (3) throws.

4. The suture of claim 1, wherein the second extension includes three (3) throws.

5. The suture of claim 1, wherein the end effector defines a substantially T-shape.

6. The suture of claim 1, wherein the end effector is formed on a distal end of the body portion.

7. A suture comprising:
a body portion having first and second ends and defining a longitudinal axis therebetween; and
an end effector integrally formed from the body portion and fixed relative to the longitudinal axis, the end effector including first and second extensions extending perpendicular to the longitudinal axis in opposite directions, wherein the first end extends in a first direction relative to the end effector and the second end extends in a second opposite direction relative to the end effector, wherein the first extension is configured substantially identically to the second extension, and wherein the first and second extensions each include a plurality of throws.

8. The suture of claim 7, wherein the end effector is formed from a single continuous end of the body portion.

9. The suture of claim 7, wherein each of the throws defines a central axis that is perpendicular to the longitudinal axis of the body portion.

* * * * *